US011674931B2

(12) United States Patent
Coutard et al.

(10) Patent No.: US 11,674,931 B2
(45) Date of Patent: Jun. 13, 2023

(54) DEVICE FOR DETECTING AN ANALYTE VIA PHOTOACOUSTIC DETECTION

(71) Applicant: COMMISSARIAT A L'ENERGIE ATOMIQUE ET AUX ENERGIES ALTERNATIVES, Paris (FR)

(72) Inventors: Jean-Guillaume Coutard, Grenoble (FR); Laurent Duraffourg, Grenoble (FR); Alain Gliere, Grenoble (FR); Alexandre Teulle, Grenoble (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 261 days.

(21) Appl. No.: 17/209,301

(22) Filed: Mar. 23, 2021

(65) Prior Publication Data

US 2021/0302387 A1   Sep. 30, 2021

(30) Foreign Application Priority Data

Mar. 24, 2020 (FR) ...................... 20 02883

(51) Int. Cl.
*G01N 29/24* (2006.01)
*G01N 29/02* (2006.01)
*G01N 33/49* (2006.01)

(52) U.S. Cl.
CPC ......... *G01N 29/2418* (2013.01); *G01N 29/02* (2013.01); *G01N 33/49* (2013.01)

(58) Field of Classification Search
CPC .... G01N 29/2418; G01N 29/02; G01N 33/49; G01N 2291/02466; G01N 21/1717;
(Continued)

(56) References Cited

U.S. PATENT DOCUMENTS

2008/0011055 A1   1/2008   Riddle
2008/0134756 A1   6/2008   Riddle
(Continued)

FOREIGN PATENT DOCUMENTS

WO   WO 2019/110084 A1   6/2019

OTHER PUBLICATIONS

French Preliminary Search Report dated Dec. 8, 2020 in Patent Application No. FR2002883 (with English translation of categories of cited documents), 11 pages.
(Continued)

*Primary Examiner* — Tarun Sinha
(74) *Attorney, Agent, or Firm* — Oblon, McClelland, Maier & Neustadt, L.L.P.

(57) ABSTRACT

Photoacoustic detecting device (1), intended to be applied, via a contact face (3), against a medium to be analysed, the device comprising:
  a hollow cavity (20) comprising a first aperture (22) produced in the contact face, the cavity being bounded by a containment shell (21) that extends around the first aperture;
  a pulsed or amplitude-modulated light source (10) configured to emit, in an emission spectral band ($\Delta\lambda$), an incident light wave (11) through the cavity (20) to the first aperture;
  an acoustic transducer (28) linked to the cavity and configured to detect a photoacoustic wave (12) extending through the cavity.
The photoacoustic detecting device is optimized to increase the amplitude of the photoacoustic wave detected by the acoustic transducer.

10 Claims, 10 Drawing Sheets

(58) Field of Classification Search
CPC ....... G01N 29/2425; G01N 2021/1731; G01N 21/1702; G01N 21/01; G01N 29/09; G01N 29/348; A61B 5/0095; A61B 5/14532

See application file for complete search history.

(56) References Cited

U.S. PATENT DOCUMENTS

2014/0073899 A1* 3/2014 Cohrs ............... A61B 5/0095
600/407
2019/0159705 A1 5/2019 Sim et al.

OTHER PUBLICATIONS

Joo Yong Sim, et al. "In vivo Microscopic Photoacoustic Spectroscopy for Non-Invasive Glucose Monitoring Invulnerable to Skin Secretion Products" Scientific Reports, vol. 8 No. 1059, 2018, pp. 1-11.

Jonas Kottmann, et al., "Mid-Infrared Photoacoustic Detection of Glucose in Human Skin: Towards Non-Invasive Diagnostics" Sensors, vol. 16, 2016, pp. 1-14.

Miguel A. Pleitez, et al., "Windowless Ultrasound Photoacoustic Cell for in vivo Mid-IR Spectroscopy of Human Epidermis: Low Interference by Changes of Air Pressure, Temperature, and Humidity Caused by Skin Contact Opens the Possibility for a Non-Invasive Monitoring of Glucose in the Interstitial Fluid" Review of Scientific Instruments, vol. 84, 2013, pp. 084901-1-084901-8 and cover page.

Jonas Kottmann, "Glucose Sensing in Human Epidermis using Mid-Infrared Photoacoustic Detection" Biomedical Optics Express, vol. 3, No. 4, Apr. 1, 2012, pp. 667-680.

Otto Hertzberg, et al., "Depth-Selective Photothermal IR Spectroscopy of Skin: Potential Application for Non-Invasive Glucose Measurement" Analyst, vol. 142, 2017, pp. 495-502.

* cited by examiner

DEVICE FOR DETECTING AN ANALYTE VIA PHOTOACOUSTIC DETECTION

TECHNICAL FIELD

The technical field of the invention is detection of an analyte using the technique of photoacoustic detection.

PRIOR ART

Photoacoustic detection is based on detection of an acoustic wave generated under the effect of absorption, by an analysed medium, of a pulsed or amplitude-modulated electromagnetic incident wave. The acoustic wave is formed following heating, under the effect of absorption of the incident wave, of absorbent molecules present in the analysed medium. The heating leads to a modulated thermal expansion of the medium, said expansion being the origin of the acoustic wave.

Photoacoustic detection may be made specific to one particular analyte, by adjusting the wavelength of the incident electromagnetic wave to an absorption wavelength of the analyte. Photoacoustic detection has thus been applied to the detection of gaseous species in a gas, or to the detection of the presence of particular molecules in biological tissues. The wavelength of the incident wave is frequently located in the infrared.

Photoacoustic detection is then a non-invasive analysis technique that may be applied to scattering or opaque media.

Applications of photoacoustic detection to biological tissues are for example described in the following publications:

Bauer AJ. "IR-spectroscopy for skin in vivo: Optimal skin sites and properties for non-invasive glucose measurement by photoacoustic and photothermal spectroscopy"; Journal of Biophotonics 11 (2018);

"Windowless ultrasound photoacoustic cell for in-vivo mid-IR spectroscopy of human epidermis: Low interference by changes of air pressure, temperature, and humidity caused by skin contact opens the possibility for a non-invasive monitoring of glucose in the interstitial fluid", Rev. Sci. Instrum. 84, 084901 (2013).

In these publications, a pulsed light source that is activated at a frequency comprised between several tens of hertz and several tens of kilohertz is employed. The objective is to estimate a glucose concentration in the interstitial bodily fluid, at a depth comprised between 10 μm and 50 μm under the skin of a user. To this end, a photoacoustic detecting device placed against the skin of a user is used.

The inventors have sought to improve existing devices, so as to make it possible to address larger depths and to increase the amplitude of the detected acoustic wave.

SUMMARY OF THE INVENTION

A first subject of the invention is a photoacoustic detecting device, intended to be applied, via a contact face, against a medium to be analysed, the device comprising:
- a hollow cavity that emerges onto a first aperture, the first aperture being produced in the contact face;
- a pulsed or amplitude-modulated light source configured to emit, in an emission spectral band, an incident light wave through the cavity to the first aperture;
- an acoustic transducer linked to the cavity and configured to detect a photoacoustic wave extending through the cavity;

such that, under the effect of illumination of the medium, by the incident light wave, the acoustic transducer detects an acoustic wave produced by heating of the medium.

The device may comprise any one of the following features, implemented alone or in any technically achievable combination:
- the light source is a laser source;
- the volume of the cavity is smaller than 50 μL (microlitres) or than 30 μL. It may be comprised between 5 μL and 30 μL.
- the device comprises an open tube extending between the cavity and the air lying outside the cavity, over a length comprised between 1 and 20 mm, the diameter of the tube being such that:
  - when the volume of the cavity is smaller than or equal to 15 μL, the diameter of the tube is comprised between 150 μm and 300 μm.
  - when the volume of the cavity is comprised between 15 μL and 30 μL, the diameter of the tube is comprised between 200 μm and 350 μm.
  - when the volume of the cavity is larger than 30 μL, the diameter of the tube is comprised between 250 μm and 500 μm.
- the cavity is bounded by a transverse wall and a lateral wall, the lateral wall extending between the transverse wall and the contact face;
- the tube extends through/from the transverse wall or through the lateral wall;
- the device comprises an acoustic channel extending between the acoustic transducer and the cavity;
- the device comprises an optical component configured to direct the incident light wave, emitted by the light source, to the first aperture, the optical component possibly being a reflector;
- the light source is a laser source, the device possibly then comprising a holder extending from the contact face to the light source, the holder being configured to conduct heat emitted by the analysed medium to the light source;
- the device comprises a holder extending from the contact face to the light source, the holder being configured to conduct heat emitted by the analysed medium to the light source. The holder comprises a thermally conductive metal, copper or aluminium for example;
- the volume of the cavity is smaller than 20 μL.

A second subject of the invention is a method for estimating a concentration of an analyte in a medium, comprising the following steps:

a) applying a device according to the first subject of the invention against a medium, such that the contact face is held against the medium;

b) activating the light source, the light source emitting, at a wavelength corresponding to an absorption wavelength of the analyte, an incident light wave that is pulsed or amplitude-modulated at an activation or modulation frequency;

c) detecting an acoustic wave emitted by the medium, under the effect of the incident light wave, at a frequency equal to the activation frequency of the light source;

d) measuring an amplitude of the acoustic wave;

e) detecting the analyte and/or estimating the concentration of the analyte in the medium from the amplitude measured in step d).

The invention will be better understood on reading the description of the exemplary embodiments, which are described, in the rest of the description, with reference to the figures listed below.

FIGURES

In FIGS. 3A, 3B and 3C, the volume of the cavity is equal to 5 μL.

In FIGS. 4A, 4B and 4C, the volume of the cavity is equal to 10 μL.

In FIGS. 5A, 5B and 5C, the volume of the cavity is equal to 20 μL.

In FIGS. 6A, 6B, 6C and 6D, the volume of the cavity is equal to 50 μL.

In FIG. 7I, the height of the tube is 19 mm and the volume of the cavity is 50 μL.

DESCRIPTION OF PARTICULAR EMBODIMENTS

Figure 1A:
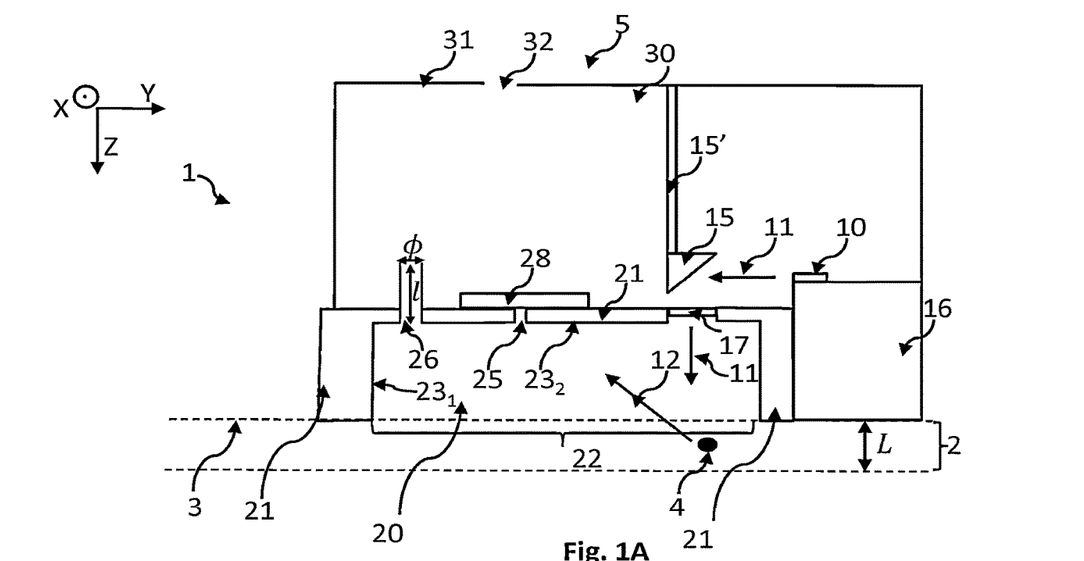
FIGS. 1A and 1B show two embodiments of a device according to the invention.

FIG. 1A schematically shows a device 1 allowing the invention to be implemented. The device 1 is configured to be applied against a medium 2 to be analysed. The device comprises a contact face 3, which is intended to be applied against the medium to be analysed. The contact face is designed to conform to the medium against which it is intended to be pressed. It is for example planar. In this example, the medium 2 is the skin of a user. The device comprises a light source 10, which is configured to emit a light wave 11 that propagates to the medium 2 to be analysed. The light source 10 is pulsed or amplitude-modulated. The light wave 11 is emitted in an emission spectral band Δλ comprising an absorption wavelength $\lambda_a$ of an analyte 4 present in the medium. One objective of the device 1 is to detect the presence of the analyte 4 and potentially to estimate a concentration thereof.

The analyte 4 may be a molecule present in a bodily fluid. It may for example be a question of glucose, or of a bodily analyte such as cholesterol, triglycerides, urea, albumin, an alcohol (ethanol for example), or tetrahydrocannabinol.

The emission spectral band preferably lies in the visible or in the infrared and for example extends between wavelengths of 3 μm and 15 μm. Preferably, the emission spectral band Δλ is narrow enough for the device 1 to be specific to a single analyte. For example, the width of the emission spectral band is of the order of 0.1 μm. When the analyte is glucose, the emission spectral band is centred on an absorption wavelength of glucose, for example a wavelength corresponding to a wavenumber of 1034 cm$^{-1}$. The light source 10 may notably be a pulsed laser source and may for example be a wavelength-tunable quantum cascade laser (QCL). The emission spectral band Δλ is then located in the infrared.

According to other embodiments, the light source may be a filament-based source or a light-emitting diode. According to these embodiments, it is preferable to associate the light source with a bandpass filter in order to define a sufficiently narrow emission spectral band centred on the absorption wavelength in question. However, recourse to a laser source is preferred.

In the embodiment shown in FIG. 1A, the device 1 comprises an optical component 15 that is configured to deviate the light wave 11 emitted by the light source towards the medium 2 to be analysed.

The device 1 is intended to be applied against a medium to be analysed 2. It comprises a containment shell 21, which is placed in contact with the medium, and which defines a cavity 20. The cavity 20 emerges onto a first aperture 22, which is produced in the contact face 3, so as to emerge onto the medium 2. The incident light wave 11, after having been reflected by the optical component 15, propagates to the medium 2 through the cavity 20, and through the first aperture 22. The device comprises a transparent window 17, which is configured to transmit the incident light wave 11.

In the device shown in FIG. 1A, the optical component 15 is a reflector, taking the form of a reflective prism. It is linked to a cover 31 of the device by a holder 15'. In other embodiments, the optical component 15 may be an optical fibre that describes a curve so that the incident light wave 11 reaches the medium 2 at a normal, or substantially normal, incidence. By substantially normal, what is meant is normal to within an angular tolerance of ±30°.

Under the effect of the presence of an analyte 4 in the medium 2, a photoacoustic wave 12 is formed. The photoacoustic wave 12 is an acoustic wave formed as a result of periodic heating of the medium by the incident light wave 11, the latter being pulsed or amplitude-modulated. Some of the photoacoustic wave 12 extends through the cavity 20 so as to be detected by an acoustic transducer 28. The acoustic transducer 28 is linked to the cavity 20 by an acoustic channel 25. The acoustic transducer may be a microphone, having a detection spectral range comprising the frequency of the photoacoustic wave.

As mentioned in the publication Kottmann "Mid-infrared photoacoustic detection of glucose in human skin: towards non-invasive diagnostics", Sensors 2016, 16, 1663 (this publication will be referred to below as "Kottmann 2016"), a relationship may be established between the amplitude A of the photoacoustic wave, at the frequency f, and the volume V of the cavity 20, such that:

$$A \propto \frac{I_{10}(\lambda)\alpha(\lambda)}{Vf^{\frac{3}{2}}} \quad (1)$$

where:
∝ indicates proportionality;
$I_{10}(\lambda)$ is the intensity of the incident light wave at the wavelength A;
$\alpha(\lambda)$ is an absorption coefficient of the analysed medium at the wavelength λ;
V is the volume of the cavity, including the acoustic channel where appropriate;

f is the frequency of the acoustic wave.

When the frequency f and the intensity $I_{10}(\lambda)$ of the light wave are set, the amplitude of the photoacoustic wave A detected by the acoustic transducer is proportional to the absorption coefficient α(λ) of the medium. The latter may be considered to be proportional to the concentration of analyte in the medium. Thus, measuring the amplitude A with the acoustic transducer 28 allows the concentration of analyte in the medium to be estimated, via estimation of the absorption coefficient α(λ) of the medium.

Expression (1) assumes that the thickness L of the medium 2 is such that:

$$L \gg \mu_a(\lambda) > \mu_s(\lambda) \quad (2)$$

where:
$\mu_a(\lambda)$ is the depth of optical penetration, $\mu_a(\lambda)$ being such that $$\mu_a(\lambda) = \frac{1}{\alpha(\lambda)} \quad (3)$$

$\mu_s(\lambda)$ is a thermal diffusion length, such that $$\mu_s(\lambda) = \left(\frac{D}{\pi f}\right)^{\frac{1}{2}} \quad (4)$$

In Expression (4), D is a coefficient of thermal diffusion, such that:

$$D = \frac{k}{\rho C} \quad (5)$$

where:
ρ is the density of the medium;
C is the heat capacity of the medium;
k is the thermal conductivity of the medium.

It may be seen that $\mu_a(\lambda)$ does not depend on the frequency f, whereas $\mu_s(\lambda)$ varies inversely with the square root of the frequency f. In "Kottman 2016", it has been established that when the medium is a biological tissue, skin for example, the condition $L \gg \mu_a(\lambda) > \mu_s(\lambda)$ is met provided that the frequency is higher than 50 Hz.

Expression (1) shows that use of low frequencies allows the amplitude of the photoacoustic wave 12 to be increased. Thus, the inventors concluded that when the medium 2 is a biological tissue, it is advantageous for the frequency of the photoacoustic wave to be lower than 1 kHz, and preferably lower than 500 Hz. It is preferably comprised between 50 Hz and 500 Hz.

From Expression (4) it will be clear that decreasing the frequency f also allows the thermal diffusion length $\mu_s(\lambda)$ to be increased. This allows the medium to be interrogated to greater depth.

When the analyte 4 is glucose, or another nutrient conveyed by the blood, increasing the depth to which the concentration of the analyte is determined is an advantage. Specifically, photoacoustic detection does not allow large depths, millimeter-scale depths for example, to be reached. However, it is at these depths that the capillaries lie. With photoacoustic detection, glucose concentration is estimated indirectly, by estimating the concentration of glucose in the interstitial fluid that lies between the capillaries and the cells of the epidermis. It has been established that the glucose concentration in the interstitial fluid follows the glucose concentration in the blood, the time lag therebetween being about 20 minutes. By increasing the depth to which the medium 2 is examined, the time lag between the glucose concentration in the blood and the concentration estimated using Expression (1) is decreased.

According to Expression (1), the volume of the cavity 20 must be small in order to increase the amplitude of the photoacoustic wave. However, the smaller the volume of the cavity, the higher the frequency f.

On account of Expression (1), a compromise must be obtained so as to decrease volume while keeping an eye on the frequency f, the objective being to increase the amplitude of the photoacoustic wave in order to improve the sensitivity of the method.

The inventors have reached a satisfactory compromise by designing a cavity 20 of small volume, comprised between 1 and 50 µL, and preferably between 5 and 30 µL. The containment shell 21 comprises a solid internal wall 23 bounding the cavity 20. The internal wall comprises:
- a lateral component $23_1$, which preferably extends parallel to a Z-axis normal to the contact face 3.
- a transverse component $23_2$, which extends parallel, or substantially parallel, to the contact face 3, facing the latter. The transverse component $23_2$ extends parallel, or substantially parallel, to the first aperture 22. In the embodiment shown in FIGS. 1A and 1B, the transverse component $23_2$ includes the window 17.

Figure 1B:
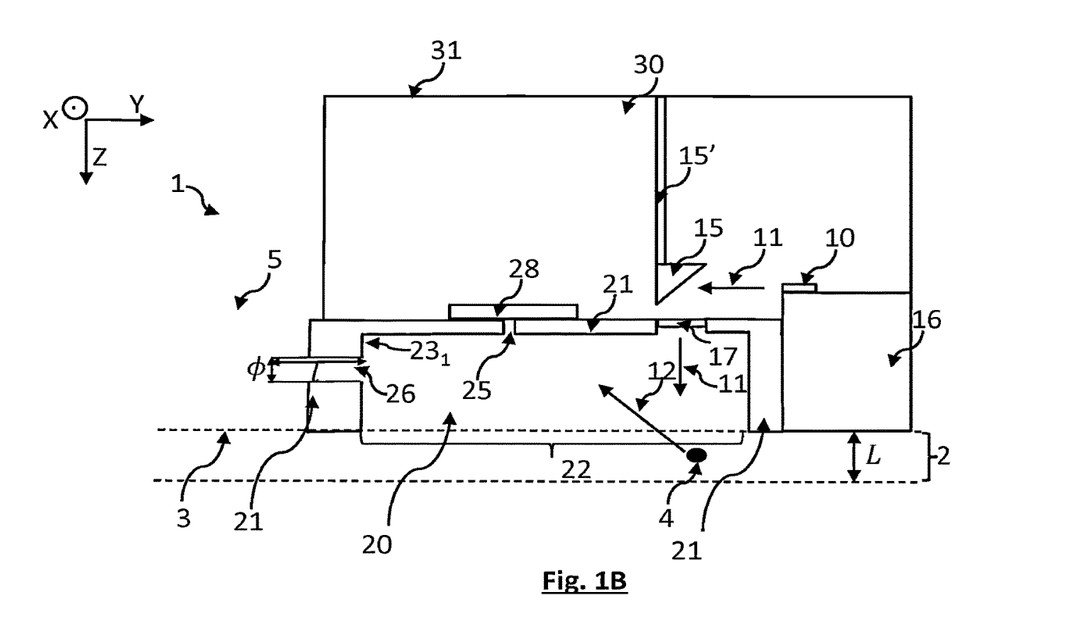

By substantially parallel, what is meant is parallel to within an angular tolerance of ±30° or ±20°. The lateral component $23_1$ extends between the contact face 3 and the transverse component $23_2$.

The device comprises a tube 26, which extends from the cavity 20 and emerges into air outside the cavity 20. The tube 26 forms an aperture through which the cavity 20 makes contact with air, at room pressure, outside the cavity. The tube 26 extends over a length l and has a cross-section of diameter ϕ. In FIG. 1A, the tube 26 extends through the transverse component $23_2$ of the internal wall. In FIG. 1B, the tube 26 extends through the lateral component $23_1$ of the internal wall.

In the configuration shown in FIG. 1A, the tube 26 emerges into a space 30, which is bounded by a cover 31. The cover 31 comprises at least one orifice 32 allowing communication with the air 5 outside of the device 1. In the configuration shown in FIG. 1B, the tube 26 emerges directly onto the air outside of the device 1. Thus, the tube 26 emerges, directly or indirectly, onto the outside air 5.

An important element of the invention is the observation, which the inventors made, that if the geometry of the tube 26 is varied, the spectral response of the cavity 20 varies. The inventors set themselves the objective of obtaining a spectral response that was as uniform as possible between 100 Hz and 1000 Hz. By spectral response, what is meant is the amplitude of the acoustic pressure in the cavity, as a function of frequency.

Figure 2A:
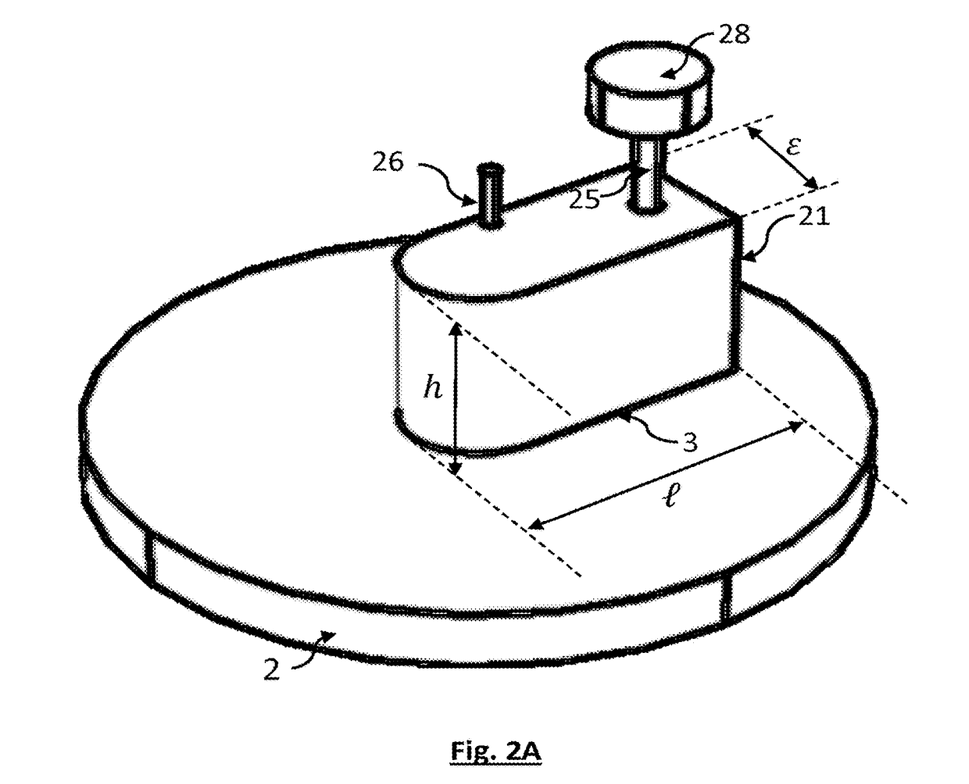
FIG. 2A shows a cavity that has been modelled.

The inventors considered a cavity such as shown in FIG. 2A. The dimensions l, ε and h shown in FIG. 2A were 2.6 mm, 1.2 mm and 1.5 mm, respectively.

It is known that such a cavity may be modelled by an equivalent circuit diagram. This allows the pressure, inside the cavity, under the effect of the presence of an acoustic wave to be simulated, as described in the publication Dehé A. et al "The Infineon Silicon MEMS microphone", AMA conferences 2013—Sensor 2013, Opto 2013.

Figure 2B:
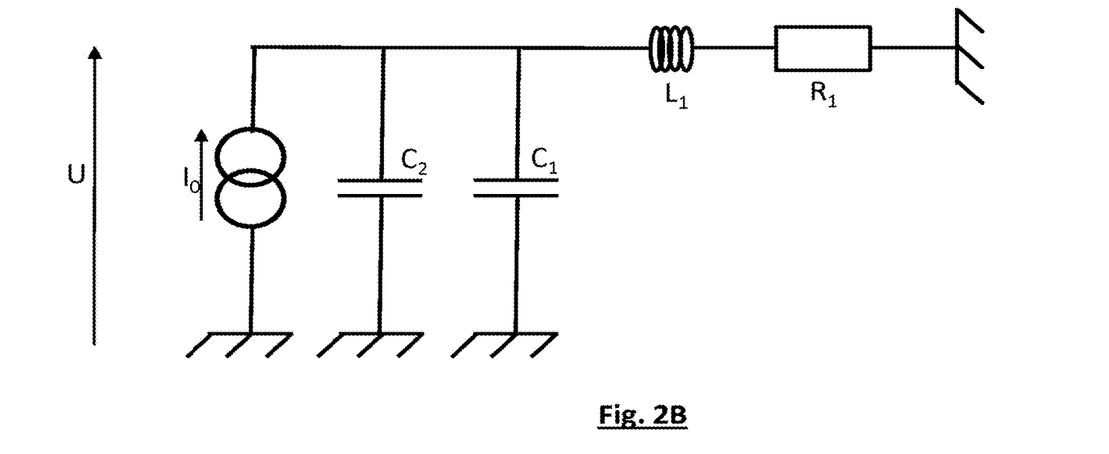
FIG. 2B shows an equivalent circuit diagram of the modelled cavity in FIG. 2A.

FIG. 2B shows an equivalent circuit diagram of the cavity shown in FIG. 2A. The excitation by an exciting acoustic wave is modelled by a current source $I_0$ that is amplitude-modulated at an excitation frequency. The response of the cavity, i.e. the amplitude of the acoustic wave in the cavity, corresponds to the voltage U, which is also amplitude-modulated at the excitation frequency.

If $P_0$ is the pressure of the acoustic wave in the cavity, the current $I_0$ depends on the power of the laser according to the expression:

$$I_0 = \frac{\gamma - 1}{\gamma} \frac{P_{laser}}{P_o} \mu_s \alpha \quad (6)$$

where γ is an adiabatic coefficient of air and $P_{laser}$ is the power of the laser.

$\mu_s$ is the thermal diffusion length described with respect to Expression (4);

α is a coefficient of absorption per unit length.

The effect of the cavity is modelled by a capacitor $C_2$, such that:

$$C_2 = \frac{V}{\gamma P_0} \quad (7)$$

where V is the volume of the cavity 20, including the acoustic channel 25 where appropriate.

The effect of the tube 26 is modelled by a capacitor $C_1$ connected in parallel to the capacitor $C_2$, and an inductor $L_1$ connected in series with a resistor $R_1$, which are such that:

$$C_1 = \frac{lS}{\gamma P_0} \quad (8)$$

where l and S correspond to the length and to the cross-sectional area of the tube 26, respectively.

$$L_1 = \frac{\rho_0 l}{S} \quad (9)$$

where $\rho_0$ corresponds to the density of air.

$$R_1 = \frac{8\pi \mu l}{S^2} \quad (10)$$

where µ corresponds to the viscosity of air.

The inventors have used the model schematically shown in FIG. 2B, while considering a laser modulation frequency comprised between $10^2$ Hz and $10^4$ Hz, and a laser power $P_{laser}$ equal to 1 mW. They have estimated the amplitude of the voltage U, which is modulated at the laser modulation frequency. It is considered to be representative of the pressure in the cavity. The computation of the voltage U, taking into account various excitation frequencies, allows a spectral response of the cavity 20 to be established.

The inventors have successively considered 4 different cavity volumes, equal to 5 µL, 10 µL, 20 µL and 50 µL, respectively. For each volume, they studied the effect of varying the diameter of the tube and its length, on the spectral response in the cavity. The performance of each modelled configuration was examined considering:

a relative pressure variation $\Delta P_0$ in the spectral band 100 Hz-1 kHz: It corresponds to the following expression:

$$\Delta P_0 = \frac{P_{0,max} - P_{0,min}}{\overline{P_0}} \quad (11)$$

where $P_{0,max}$, $P_{0,min}$ and $\overline{P_0}$ are the maximum pressure, the minimum pressure and the average pressure in the spectral band 100 Hz-1 kHz, respectively. The objective is to obtain the smallest possible relative pressure variation.

an average pressure normalized by an average pressure obtained when a closed cavity, i.e. a cavity without a tube 26, is used. The normalized average pressure is denoted $\overline{P_{0,N}}$. It is such that:

$$\overline{P_{0,N}} = \frac{\overline{P_0}}{\overline{P_{0,C}}} \quad (12)$$

where $\overline{P_0}$ and $\overline{P_{0,C}}$ are the average pressure in the modelled cavity, in the spectral band 100 Hz-1 kHz, and the average pressure, in a cavity of same size, but closed, in the same spectral band, respectively. The normalized average pressure represents the magnitude of the detected signal, and corresponds to an indicator of the sensitivity of the measurement. It is preferable for it to be as high as possible.

To determine $\Delta P_0$ and $\overline{P_{0,N}}$, the inventors modelled a cavity such as described with reference to FIG. 2A. They considered various volumes and, for each volume, various tube dimensions: in particular a diameter varying between 50 μm and 500 μm and a length varying between 1 mm and 10 mm. They modelled the cavity using the circuit diagram described with reference to FIG. 2B. They estimated the voltage U, which is representative of the pressure $P_0$, for various frequencies comprised between 100 Hz and 10 kHz. On the basis of this modelling, they estimated the quantities $\Delta P_0$ and $\overline{P_{0,N}}$ described with reference to Expressions (11) and (12), these quantities being considered to be performance indicators.

Figure 3A:
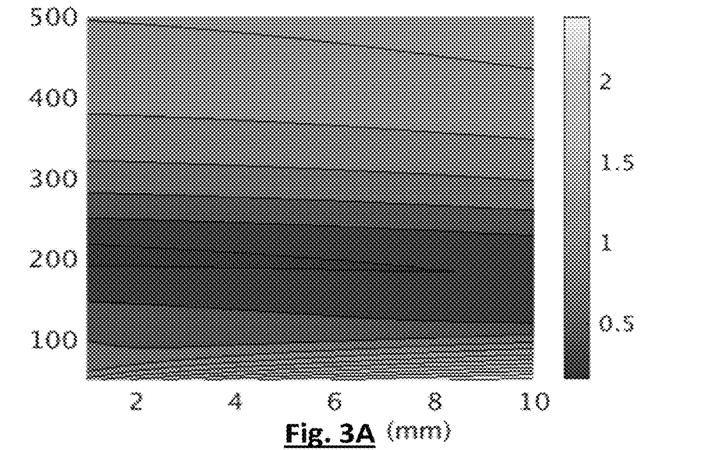
FIG. 3A shows the results of modelling a relative variation in the amplitude of an acoustic wave in a cavity such as illustrated in FIG. 2A, in the spectral band 100 Hz-1 kHz, as a function of the length of the emergent tube of the cavity (x-axis—mm), and of the diameter of the latter (y-axis—μm).
Figure 3B:
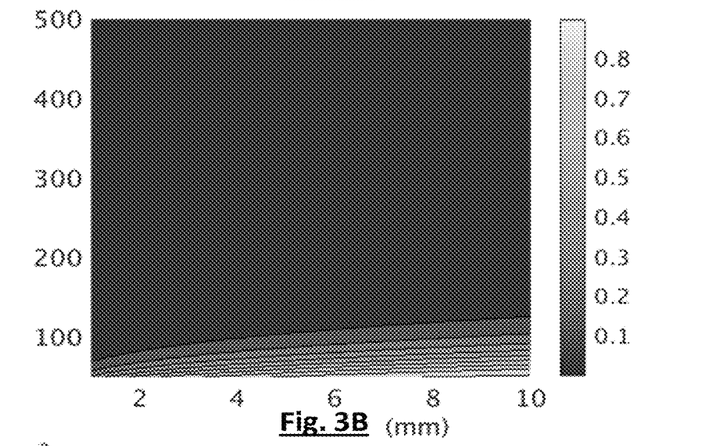
FIG. 3B shows the results of modelling a normalized average amplitude of an acoustic wave in a cavity such as illustrated in FIG. 2A, in the spectral band 100 Hz-1 kHz, as a function of the length of the emergent tube of the cavity (x-axis—mm), and of the diameter of the latter (y-axis—μm).
Figure 3C:
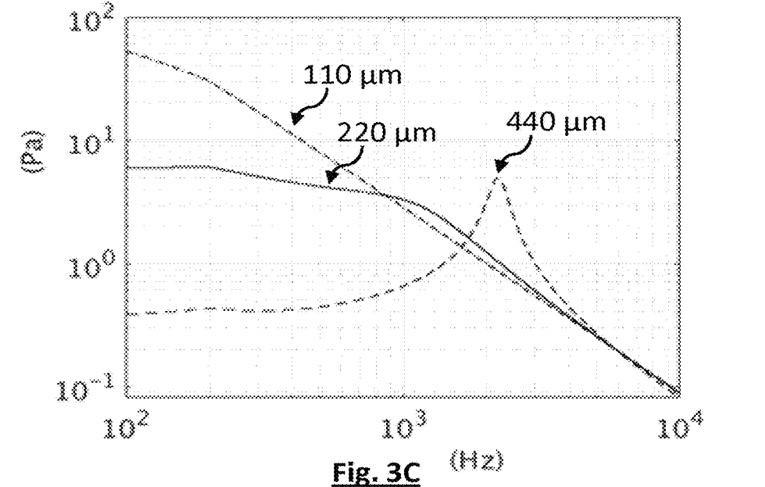
FIG. 3C shows a variation in an amplitude of an acoustic wave (y-axis) in the cavity such as illustrated in FIG. 2A, as a function of frequency (x-axis), for various configurations of the emergent tube of the cavity schematically shown in FIG. 2A and modelled by the electrical circuit shown in FIG. 2B.

FIGS. 3A and 3B show the relative pressure variation $\Delta P_0$ and the normalized average pressure $\overline{P_{0,N}}$ as a function of the length of the tube 26 (x-axis-units mm) and the diameter of the tube (y-axis-units μm), respectively. The volume of the cavity is 5 μL. In each figure, the value of the quantity in question corresponds to the greyscale level. FIG. 3C shows the spectral response modelled considering a cavity volume equal to 5 μL, the length of the tube being 10 mm, for various tube diameters, equal to 110 μm, 220 μm and 440 μm, respectively. It may be seen that an optimal performance (low $\Delta P_0$ value and high $\overline{P_{0,N}}$ value) is obtained when the length of the tube is greater than 3 mm or 5 mm and the diameter of the tube is comprised between 150 μm and 300 μm.

The analysis of FIG. 3C shows that when the diameter of the tube is small (110 μm), the spectral response is close to that of a closed cavity. When the diameter reaches 220 μm, the spectral response may be considered to be relatively "flat", i.e. uniform in a spectral band comprised between 100 Hz and 1000 Hz, this corresponding to the sought objective. The value of the pressure $P_0$ is sufficiently high to be easily measurable. When the diameter is further increased (360 μm), the spectral response of the cavity approaches that of a resonant cavity, with the appearance of a resonant peak. The value of the pressure $P_0$ decreases, this making it more difficult to measure.

Figure 4A:
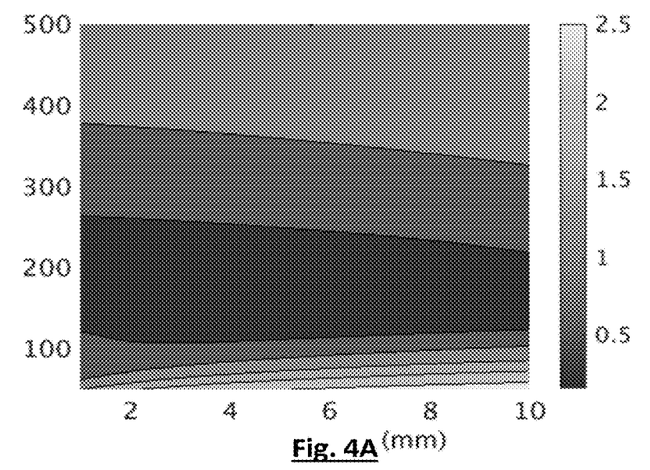
FIG. 4A shows the results of modelling a relative variation in the amplitude of an acoustic wave in a cavity such as illustrated in FIG. 2A, in the spectral band 100 Hz-1 kHz, as a function of the length of the emergent tube of the cavity (x-axis—mm), and of the diameter of the latter (y-axis—μm).
Figure 4B:
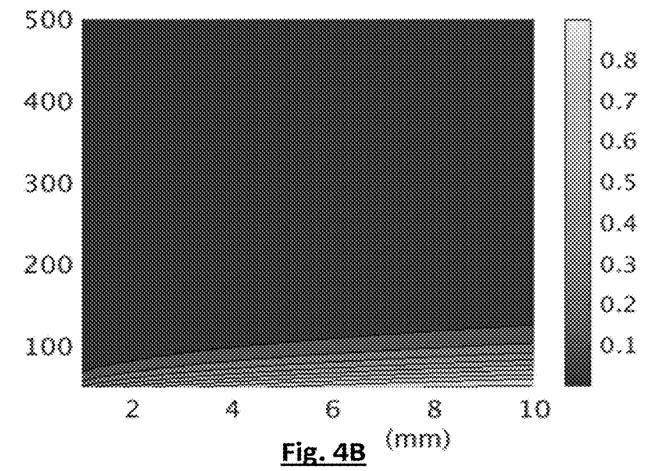
FIG. 4B shows the results of modelling a normalized average amplitude of an acoustic wave in a cavity such as illustrated in FIG. 2A, in the spectral band 100 Hz-1 kHz, as a function of the length of the emergent tube of the cavity (x-axis—mm), and of the diameter of the latter (y-axis—μm).
Figure 4C:
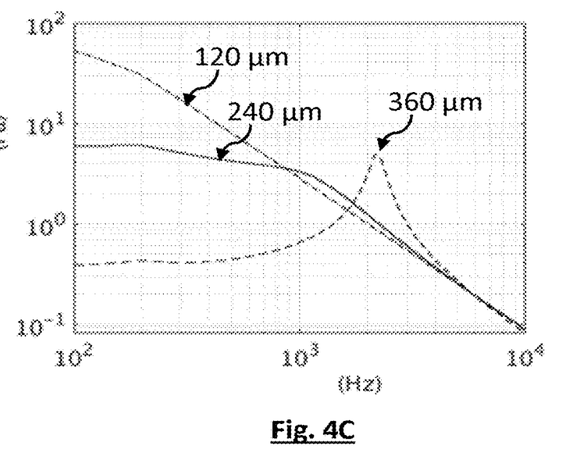
FIG. 4C shows a variation in an amplitude of an acoustic wave (y-axis) in the cavity such as illustrated in FIG. 2A, as a function of frequency (x-axis), for various configurations of the emergent tube of the cavity schematically shown in FIG. 2A and modelled by the electrical circuit shown in FIG. 2B.

FIGS. 4A, 4B and 4C are similar to FIGS. 3A, 3B and 3C, respectively, the cavity volume taken into account however being equal to 10 μL. In FIG. 4C, the diameters of the tubes in question are 120 μm, 240 μm and 360 μm, the length being 9.4 mm. It may be deduced therefrom that an optimal performance (low $\Delta P_0$ value and high $\overline{P_{0,N}}$ value) is obtained when the length of the tube is greater than 3 mm or 5 mm and the diameter of the tube is comprised between 150 μm and 300 μm.

Figure 5A:
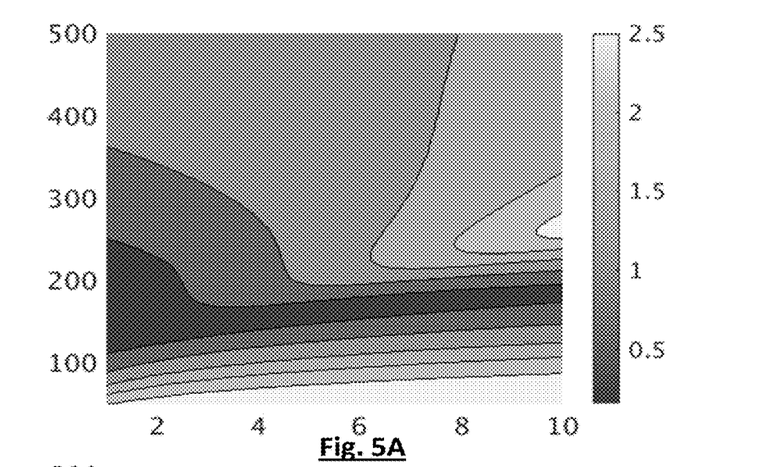
FIG. 5A shows the results of modelling a relative variation in the amplitude of an acoustic wave in a cavity such as illustrated in FIG. 2A, in the spectral band 100 Hz-1 kHz, as a function of the length of the emergent tube of the cavity (x-axis—mm), and of the diameter of the latter (y-axis—μm).
Figure 5B:
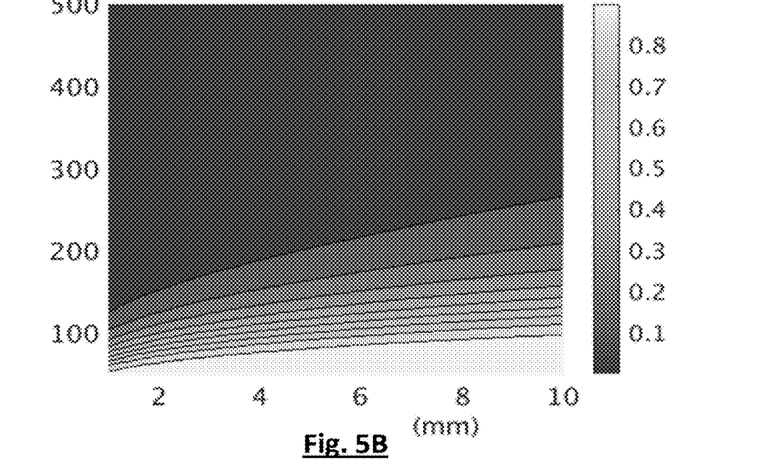
FIG. 5B shows the results of modelling a normalized average amplitude of an acoustic wave in a cavity such as illustrated in FIG. 2A, in the spectral band 100 Hz-1 kHz, as a function of the length of the emergent tube of the cavity (x-axis—mm), and of the diameter of the latter (y-axis—μm).
Figure 5C:
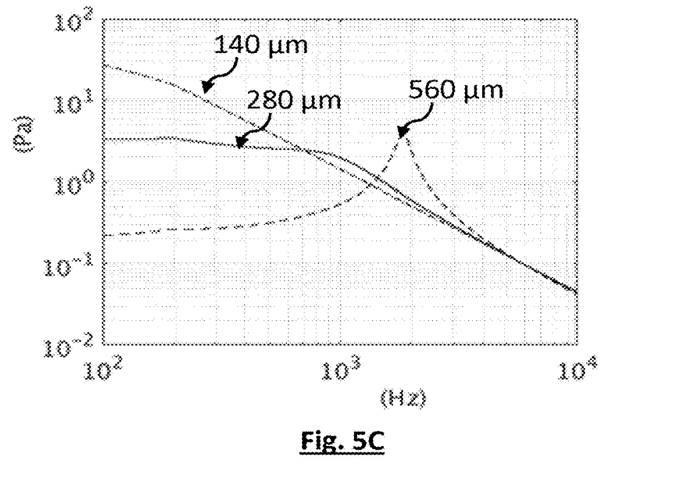
FIG. 5C shows a variation in an amplitude of an acoustic wave (y-axis) in the cavity such as illustrated in FIG. 2A, as a function of frequency (x-axis), for various configurations of the emergent tube of the cavity schematically shown in FIG. 2A and modelled by the electrical circuit shown in FIG. 2B.

FIGS. 5A, 5B and 5C are similar to FIGS. 3A, 3B and 3C, respectively, the cavity volume taken into account however being equal to 20 μL. In FIG. 5C, the diameters of the tubes in question are 140 μm, 280 μm and 560 μm, the length being 9.6 mm. It may be deduced therefrom that an optimal performance (low $\Delta P_0$ value and high $\overline{P_{0,N}}$ value) is obtained when the length of the tube is greater than 2 mm or 5 mm and the diameter of the tube is comprised between 200 μm and 350 μm.

Figure 6A:
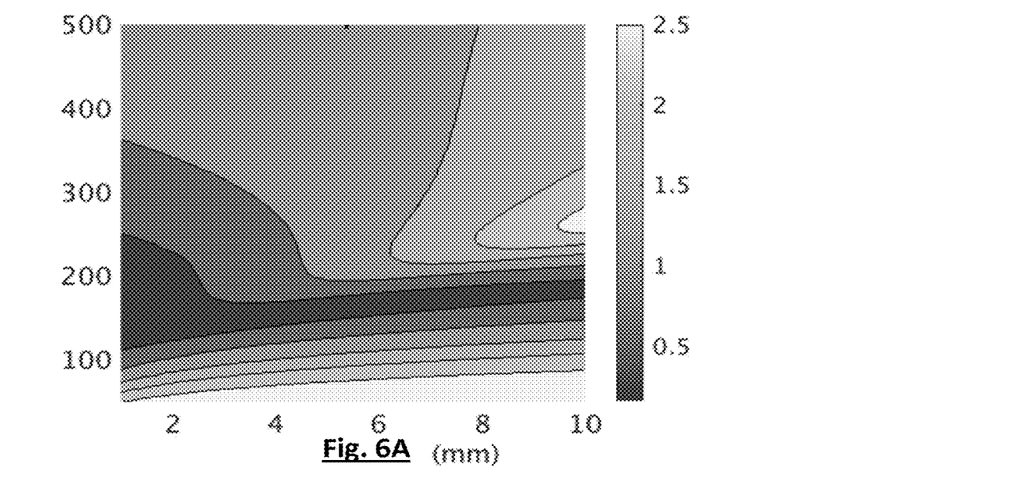
FIG. 6A shows the results of modelling a relative variation in the amplitude of an acoustic wave in a cavity such as illustrated in FIG. 2A, in the spectral band 100 Hz-1 kHz, as a function of the length of the emergent tube of the cavity (x-axis—mm), and of the diameter of the latter (y-axis—μm).
Figure 6B:
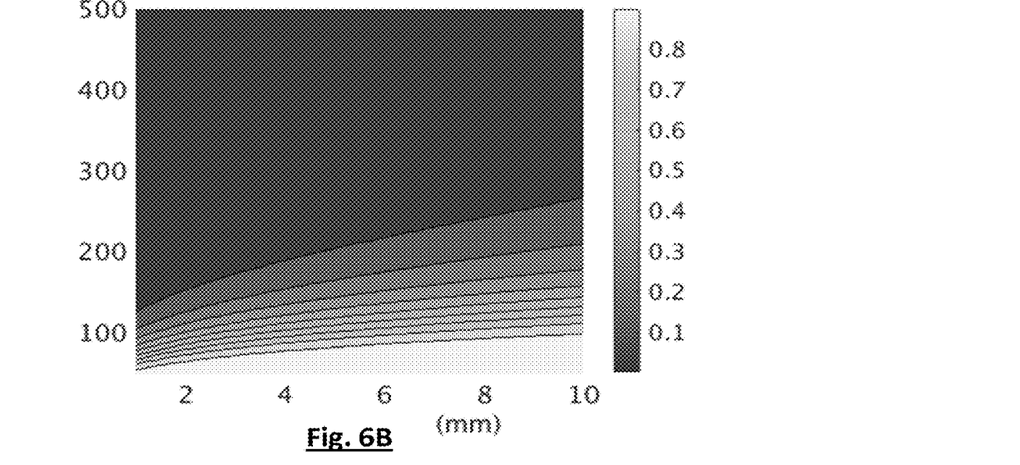
FIG. 6B shows the results of modelling a normalized average amplitude of an acoustic wave in a cavity such as illustrated in FIG. 2A, in the spectral band 100 Hz-1 kHz, as a function of the length of the emergent tube of the cavity (x-axis—mm), and of the diameter of the latter (y-axis—μm).
Figure 6C:
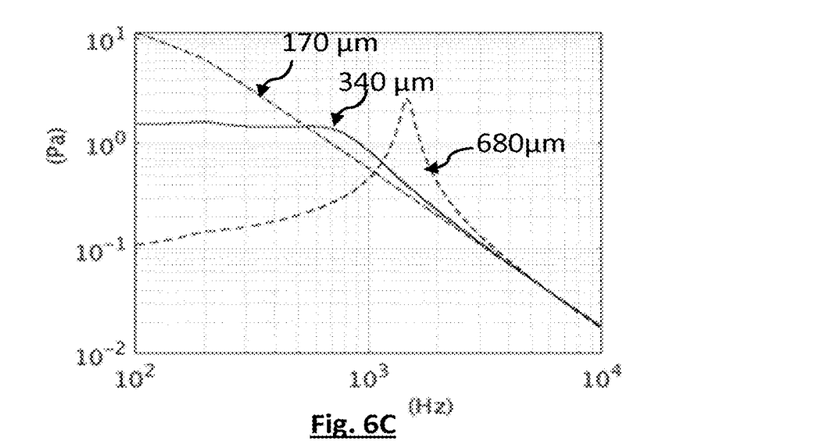
FIGS. 6C and 6D show a variation in an amplitude of an acoustic wave (y-axis) in the cavity such as illustrated in FIG. 2A, as a function of frequency (x-axis), for various configurations of the emergent tube of the cavity schematically shown in FIG. 2A and modelled by the electrical circuit shown in FIG. 2B.
Figure 6D:
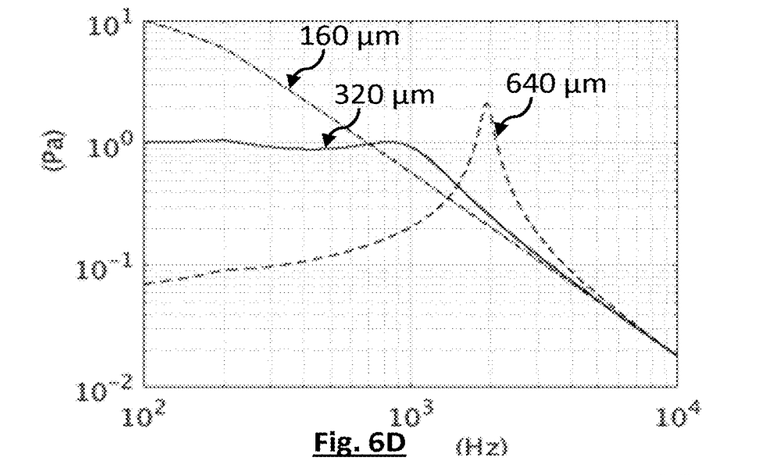

FIGS. 6A, 6B and 6C are similar to FIGS. 3A, 3B and 3C, respectively, the cavity volume taken into account however being equal to 50 μL. In FIG. 6C, the diameters of the tubes in question are 170 μm, 340 μm and 680 μm, the length being 9.4 mm. FIG. 6D shows the spectral response modelled considering a cavity volume equal to 50 μL, the length of the tube being 5 mm, for various tube diameters, equal to 160 μm, 320 μm and 640 μm, respectively.

It may be deduced from FIGS. 6A to 6D that an optimal performance (low $\Delta P_0$ value and high $\overline{P_{0,N}}$ value) is obtained when the length of the tube is greater than 1 mm or 5 mm and the diameter of the tube is comprised between 250 μm and 500 μm.

Figure 7A:
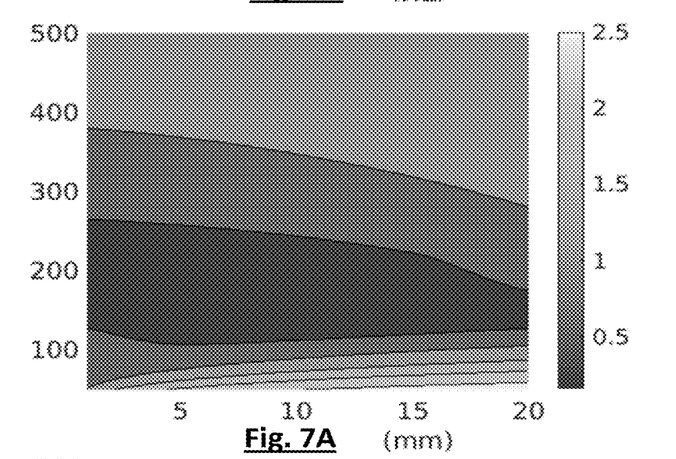
FIGS. 7A, 7B, 7C, 7D, 7E, 7F, 7G and 7H are similar to FIGS. 3A, 3B, 4A, 4B, 5A, 5B, 6A and 6B, respectively, but address a larger tube-length range (variation between 0 mm and 20 mm).
Figure 7B:
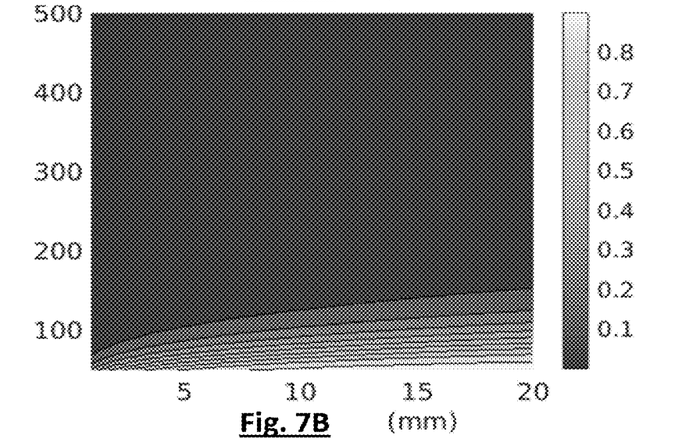
Figure 7C:
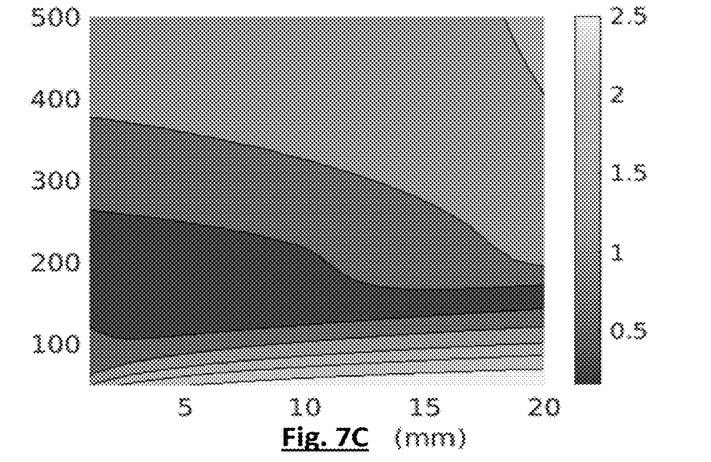
Figure 7D:
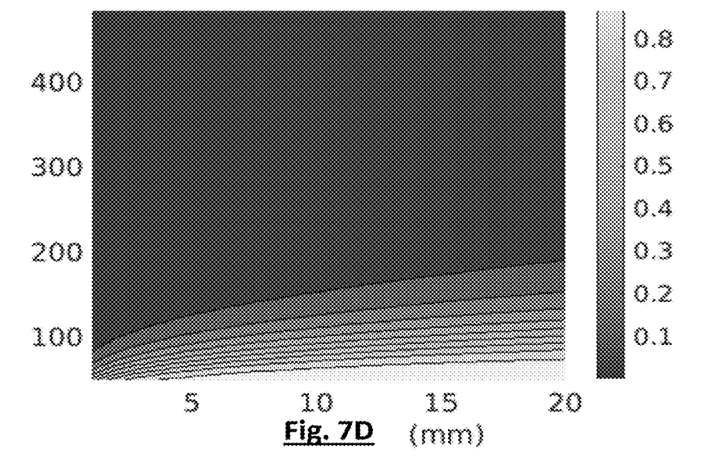
Figure 7E:
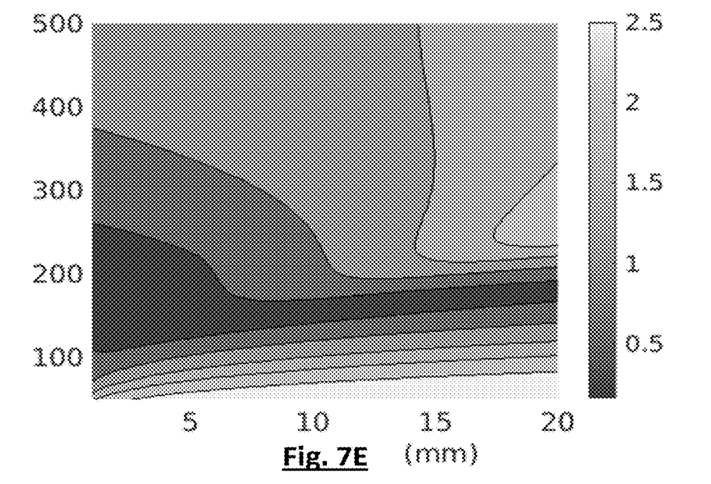
Figure 7F:
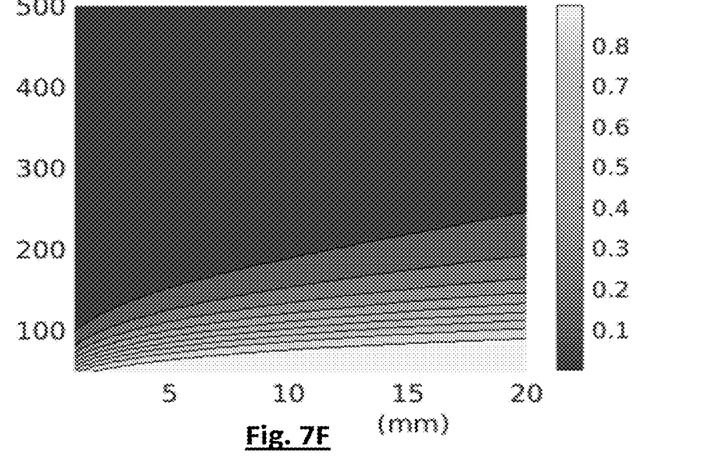
Figure 7G:
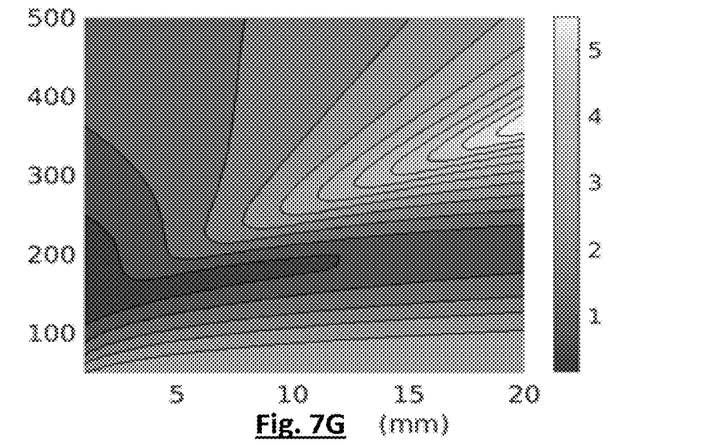
Figure 7H:
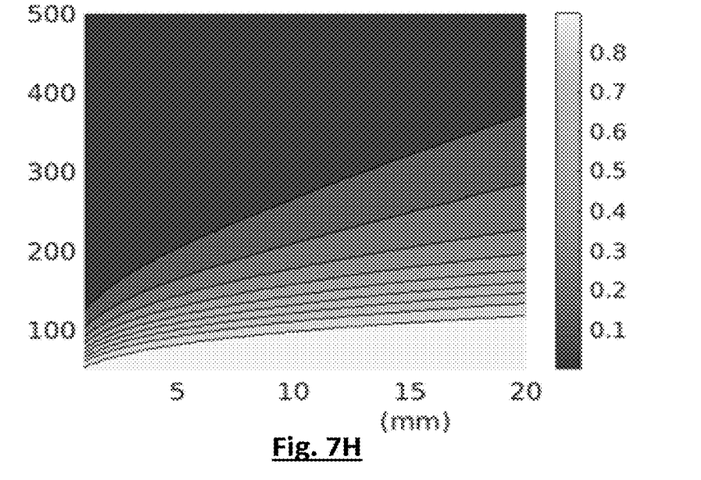
Figure 7I:
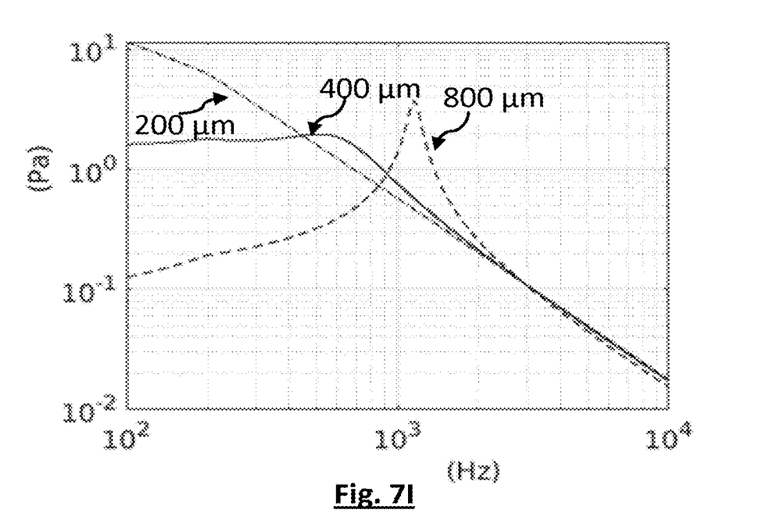
FIG. 7I shows a variation in an amplitude of an acoustic wave (y-axis) in the cavity such as illustrated in FIG. 2A, as a function of frequency (x-axis), for various configurations of the emergent tube of the cavity schematically shown in FIG. 2A and modelled by the electrical circuit shown in FIG. 2B.

FIGS. 7A, 7B, 7C, 7D, 7E, 7F, 7G and 7H are similar to FIGS. 3A, 3B, 4A, 4B, 5A, 5B, 6A and 6B, respectively, but address a larger tube-length range (variation between 0 mm and 20 mm). These figures show that the ranges of tube-diameter values defined above apply up at least to a tube length l of 20 mm. FIG. 7I shows the spectral response modelled considering a cavity volume equal to 50 μL, the length of the tube being 19 mm, for various tube diameters, equal to 200 μm, 400 μm and 800 μm, respectively. Just as was the case for FIGS. 6C and 6D, it may be seen that an optimal performance (low $\Delta P_0$ value and high $\overline{P_{0,N}}$ value) is obtained when the length of the tube is 19 mm, for a tube diameter comprised between 250 μm and 500 μm.

Generally, whatever the volume in question, when the diameter of the tube is small, the spectral response is close to that of a closed cavity. When the diameter of the tube is large, the spectral response of the cavity approaches that of a resonant cavity, with the appearance of a resonant peak. The aforementioned diameter and length ranges corresponding to a relatively flat spectral response, between the spectral response of a closed cavity and the spectral response of a resonant cavity.

Based on the modelling performed, the inventors have determined, for various cavity-volume ranges, the optimal dimensions of the tube:

When the volume of the cavity is smaller than or equal to 15 μL, the diameter of the tube may be comprised between 150 μm and 300 μm.

When the volume of the cavity is comprised between 15 μL and 30 μL, the diameter of the tube may be comprised between 200 μm and 350 μm.

When the volume of the cavity is larger than 30 µL, the diameter of the tube may be comprised between 250 µm and 500 µm.

Whatever the volume, the length of the tube is preferably greater than 1 mm or than 3 mm. It is preferably less than 20 mm.

In the embodiment shown in FIGS. 1A and 1B, the light source 10 is a QCL laser source formed on a substrate. For reasons of design simplicity, it is preferable for the light wave emitted by the light source to extend parallel to the plane of the substrate in which said wave is formed. The device comprises an optical component 15 for directing all or some of the incident light wave 11 towards the first aperture 22. The optical component may be a reflector or an optical fibre.

The optimal operating temperature of QCL laser sources is generally comprised between 30° C. and 40° C. When the device is applied against the skin of a living user, the body heat of the user may be used by way of heat source of the QCL laser source. The device then comprises a holder 16, against which the laser source 10 is placed. The holder 16 is configured to make contact with the skin of the user. The holder is made of a material having good properties as regards thermal conduction, of a metal for example, and notably of copper or of aluminium. The holder 16 extends between the contact face 3 and the light source 10. The thickness of the holder 16, along the Z-axis, is for example comprised between 1 mm and 10 mm. The holder 16 thus acts as thermal buffer, between the skin of the user and the light source.

The invention will possibly be employed to detect the presence of an analyte in a medium, the latter possibly being the skin of the user. To do this, the following steps will be applied:
- applying the device against a medium, such that the contact face is held against the medium;
- activating the light source at an activation frequency or a modulation frequency;
- detecting a photoacoustic wave emitted by the medium, under the effect of the incident light wave, at an acoustic frequency equal to the activation or modulation frequency of the light source;
- measuring an amplitude of the acoustic wave, this amounting to estimating the amplitude A described with reference to Expression (1);
- detecting the presence of the analyte and/or estimating the concentration of the analyte in the medium from the measured amplitude. This step is carried out by estimating the absorption coefficient α described with reference to Expression (1), the relationship between the analyte concentration and the absorption coefficient being known.

The invention claimed is:

1. A photoacoustic detecting device, intended to be applied, via a contact face, against a medium to be analysed, the device comprising:
 a hollow cavity that emerges onto a first aperture, the first aperture being produced in the contact face;
 a pulsed or amplitude-modulated light source configured to emit, in an emission spectral band, an incident light wave, through the cavity, to the first aperture;
 an acoustic transducer linked to the cavity and configured to detect a photoacoustic wave extending through the cavity;
 such that, under the effect of illumination of the medium, by the incident light wave, the acoustic transducer detects an acoustic wave produced by heating of the medium;
 wherein:
 the volume of the cavity is smaller than 50 µL;
 the device comprises an open tube extending between the cavity and air lying outside the cavity, over a length and a diameter, the length of the tube being comprised between 1 and 20 mm, the diameter of the tube being such that:
  when the volume of the cavity is smaller than or equal to 15 µL, the diameter of the tube is comprised between 150 µm and 300 µm;
  when the volume of the cavity is comprised between 15 µL and 30 µL, the diameter of the tube is comprised between 200 µm and 350 µm;
  when the volume of the cavity is larger than 30 µL, the diameter of the tube is comprised between 250 µm and 500 µm.

2. The device according to claim 1, wherein:
 the cavity is bounded by a transverse wall and a lateral wall, the lateral wall extending between the transverse wall and the contact face;
 the tube extends through the transverse wall or through the lateral wall.

3. The device according to claim 1, comprising an acoustic channel extending between the acoustic transducer and the cavity.

4. The device according to claim 1, comprising an optical component, configured to direct the incident light wave, emitted by the light source, to the first aperture.

5. The device according to claim 4, wherein the optical component is a reflector.

6. The device according to claim 1, wherein the light source is a laser source.

7. The device according to claim 6, the device comprising a holder extending from the contact face to the light source, the holder being configured to conduct heat emitted by the analysed medium to the light source.

8. The device according to claim 7, wherein the holder comprises a thermally conductive metal, copper or aluminium for example.

9. The device according to claim 1, wherein the volume of the cavity is smaller than 20 µL.

10. A method for estimating a concentration of analyte in a medium, comprising:
 a) applying a device according to claim 1 against a medium, such that the contact face is held against the medium;
 b) activating the light source, the light source emitting, at a wavelength corresponding to an absorption wavelength of the analyte, an incident light wave that is pulsed or amplitude-modulated at an activation or modulation frequency;
 c) detecting an acoustic wave emitted by the medium, under the effect of the incident light wave, at an acoustic frequency equal to the activation frequency of the light source;
 d) measuring an amplitude of the acoustic wave;
 e) detecting the presence of analyte and/or estimating the concentration of the analyte in the medium from the amplitude measured in d).

* * * * *